(12) United States Patent
Kadyk et al.

(10) Patent No.: US 8,067,181 B2
(45) Date of Patent: Nov. 29, 2011

(54) MELKS AS MODIFIERS OF THE RAC PATHWAY AND METHODS OF USE

(75) Inventors: Lisa Kadyk, San Francisco, CA (US); George Ross Francis, Pacifica, CA (US); Kim Lickteig, San Mateo, CA (US); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 1023 days.

(21) Appl. No.: 10/567,765

(22) PCT Filed: Aug. 12, 2004

(86) PCT No.: PCT/US2004/026231
§ 371 (c)(1),
(2), (4) Date: Sep. 14, 2006

(87) PCT Pub. No.: WO2005/016279
PCT Pub. Date: Feb. 24, 2005

(65) Prior Publication Data
US 2008/0293044 A1    Nov. 27, 2008

Related U.S. Application Data

(60) Provisional application No. 60/495,193, filed on Aug. 14, 2003.

(51) Int. Cl.
*G01N 33/53*    (2006.01)

(52) U.S. Cl. .......... 435/7.1; 435/7.2; 435/7.91; 436/518

(58) Field of Classification Search ........................ None
See application file for complete search history.

(56) References Cited

U.S. PATENT DOCUMENTS
2003/0198972 A1    10/2003    Erlander et al.

OTHER PUBLICATIONS

Heyer et al., "Expression of *Melk*, a New Protein Kinase, During Early Mouse Development," *Developmental Dynamics*, 215:344-351 (1999).
Heyer et al., "New Member of the Snf1/AMPK Kinase Family, *Melk*, Is Expressed in the Mouse Egg and Preimplantation Embryo," *Molecular Reproduction and Development*, 47:148-156 (1997).
International Search Report for PCT/US04/26231 mailed May 23, 2005.
Vulsteke et al., "Inhibition of Spliceosome Assembly by the Cell Cycle-regulated Protein Kinase MELK and Involvement of Splicing Factor NIPP1," *The Journal of Biological Chemistry*, 279(10):8642-8647 (2004).
Heyer, B.S. et al.: "Expression of MELK, a New Protein Kinase, During Early Mouse Development," Developmental Dynamics Wiley-Liss, Inc., New York, NY, US, vol. 215, No. 4, Aug. 1999, pp. 344-351.
Heyer, B.S., et al.: "New Member of the SNF1/AMPK Kinase Family, MELK, Is Expressed in the Mouse Egg and Preimplantation Embryo," Molecular Reproduction and Development, LISS, New York, NY, US, vol. 47, No. 2, 1997, pp. 148-156.

*Primary Examiner* — Jacob Cheu
(74) *Attorney, Agent, or Firm* — McDonnell Boehnen Hulbert & Berghoff LLP

(57) ABSTRACT

Human MELK genes are identified as modulators of the RAC pathway, and thus are therapeutic targets for disorders associated with defective RAC function. Methods for identifying modulators of RAC, comprising screening for agents that modulate the activity of MELK are provided.

12 Claims, No Drawings

_US 8,067,181 B2_

MELKS AS MODIFIERS OF THE RAC PATHWAY AND METHODS OF USE

REFERENCE TO RELATED APPLICATIONS

This application is a U.S. National Stage Application of PCT/US04/26231, filed Aug. 12, 2004, which claims priority to U.S. provisional patent application 60/495,193 filed Aug. 14, 2003. The contents of the prior applications are hereby incorporated by reference in their entireties.

BACKGROUND OF THE INVENTION

Cell movement is an important part of normal developmental and physiological processes (e.g. epiboly, gastrulation and wound healing), and is also important in pathologies such as tumor progression and metastasis, angiogenesis, inflammation and atherosclerosis. The process of cell movement involves alterations of cell-cell and cell-matrix interactions in response to signals, as well as rearrangement of the actin and microtubule cytoskeletons. The small GTPases of the Rho/Rac family interact with a variety of molecules to regulate the processes of cell motility, cell-cell adhesion and cell-matrix adhesion. Cdc42 and Rac are implicated in the formation of filopodia and lamellipodia required for initiating cell movement, and Rho regulates stress fiber and focal adhesion formation. Rho/Rac proteins are effectors of cadherin/catenin-mediated cell-cell adhesion, and function downstream of integrins and growth factor receptors to regulate cytoskeletal changes important for cell adhesion and motility.

There are five members of the Rho/Rac family in the _C. elegans_ genome. rho-1 encodes a protein most similar to human RhoA and RhoC, cdc-42 encodes an ortholog of human Cdc42, and ced-10, mig-2 and rac-2 encode Rac-related proteins. ced-10, mig-2 and rac-2 have partially redundant functions in the control of a number of cell and axonal migrations in the worm, as inactivation of two or all three of these genes causes enhanced migration defects when compared to the single mutants. Furthermore, ced-10; mig-2 double mutants have gross morphological and movement defects not seen in either single mutant, possibly as a secondary effect of defects in cell migration or movements during morphogenesis. These defects include a completely penetrant uncoordinated phenotype, as well as variably penetrant slow-growth, vulval, withered tail, and sterility defects, none of which are seen in either single mutant.

MELK (maternal embryonic leucine zipper kinase) is a member of the evolutionarily conserved KIN1/PAR-1/MARK kinase family which is involved in cell polarity and microtubule dynamics.

The ability to manipulate the genomes of model organisms such as _C. elegans_ provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Dulubova I, et al, J Neurochem 2001 April; 77(1):229-38; Cai T, et al., Diabetologia 2001 January; 44(1):81-8; Pasquinelli A E, et al., Nature. 2000 Nov. 2; 408(6808):37-8; Ivanov I P, et al., EMBO J 2000 Apr. 17; 19(8):1907-17; Vajo Z et al., Mamm Genome 1999 October; 10(10):1000-4). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as RAC, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the RAC pathway in _C. elegans_, and identified their human orthologs, hereinafter referred to as Maternal Embryonic Leucine Zipper Kinase (MELK). The invention provides methods for utilizing these RAC modifier genes and polypeptides to identify MELK-modulating agents that are candidate therapeutic agents that can be used in the treatment of disorders associated with defective or impaired RAC function and/or MELK function. Preferred MELK-modulating agents specifically bind to MELK polypeptides and restore RAC function. Other preferred MELK-modulating agents are nucleic acid modulators such as antisense oligomers and RNAi that repress MELK gene expression or product activity by, for example, binding to and inhibiting the respective nucleic acid (i.e. DNA or mRNA).

MELK modulating agents may be evaluated by any convenient in vitro or in vivo assay for molecular interaction with a MELK polypeptide or nucleic acid. In one embodiment, candidate MELK modulating agents are tested with an assay system comprising a MELK polypeptide or nucleic acid. Agents that produce a change in the activity of the assay system relative to controls are identified as candidate RAC modulating agents. The assay system may be cell-based or cell-free. MELK-modulating agents include MELK related proteins (e.g. dominant negative mutants, and biotherapeutics); MELK-specific antibodies; MELK-specific antisense oligomers and other nucleic acid modulators; and chemical agents that specifically bind to or interact with MELK or compete with MELK binding partner (e.g. by binding to a MELK binding partner). In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate RAC pathway modulating agents are further tested using a second assay system that detects changes in the RAC pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the RAC pathway, such as an angiogenic, apoptotic, or cell proliferation disorder (e.g. cancer).

The invention further provides methods for modulating the MELK function and/or the RAC pathway in a mammalian cell by contacting the mammalian cell with an agent that specifically binds a MELK polypeptide or nucleic acid. The agent may be a small molecule modulator, a nucleic acid modulator, or an antibody and may be administered to a mammalian animal predetermined to have a pathology associated with the RAC pathway.

DETAILED DESCRIPTION OF THE INVENTION

A genetic screen was designed to identify modifiers of the Rac signaling pathway that also affect cell migrations in *C. elegans*, where various specific genes were silenced by RNA inhibition (RNAi) in a ced-10; mig-2 double mutant background. The 4B260 gene was identified as a modifier of the RAC pathway. Accordingly, vertebrate orthologs of this modifier, and preferably the human orthologs, MELK genes (i.e., nucleic acids and polypeptides) are attractive drug targets for the treatment of pathologies associated with a defective RAC signaling pathway, such as cancer.

In vitro and in vivo methods of assessing MELK function are provided herein. Modulation of the MELK or their respective binding partners is useful for understanding the association of the RAC pathway and its members in normal and disease conditions and for developing diagnostics and therapeutic modalities for RAC related pathologies. MELK-modulating agents that act by inhibiting or enhancing MELK expression, directly or indirectly, for example, by affecting a MELK function such as enzymatic (e.g., catalytic) or binding activity, can be identified using methods provided herein. MELK modulating agents are useful in diagnosis, therapy and pharmaceutical development.

Nucleic Acids and Polypeptides of the Invention

Sequences related to MELK nucleic acids and polypeptides that can be used in the invention are disclosed in Genbank (referenced by Genbank identifier (GI) number) as GI#s 7661973 (SEQ ID NO:1), 15559348 (SEQ ID NO:2), and 33878460 (SEQ ID NO:5) for nucleic acid, and GI#7661974 (SEQ ID NO:6) for polypeptide. Additionally, nucleic acid sequences of SEQ ID NO:3 and SEQ ID NO:4 can also be used in the invention.

The term "MELK polypeptide" refers to a full-length MELK protein or a functionally active fragment or derivative thereof. A "functionally active" MELK fragment or derivative exhibits one or more functional activities associated with a full-length, wild-type MELK protein, such as antigenic or immunogenic activity, enzymatic activity, ability to bind natural cellular substrates, etc. The functional activity of MELK proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active MELK polypeptide is a MELK derivative capable of rescuing defective endogenous MELK activity, such as in cell based or animal assays; the rescuing derivative may be from the same or a different species. For purposes herein, functionally active fragments also include those fragments that comprise one or more structural domains of a MELK, such as a kinase domain or a binding domain. Protein domains can be identified using the PFAM program (Bateman A., et al., Nucleic Acids Res, 1999, 27:260-2). For example, the kinase domain (PFAM 00069) of MELK from GI#7661974 (SEQ ID NO:6) is located at approximately amino acid residues 11-263. Further, the kinase associated domain 1 (PF02149) of the same protein is located approximately at amino acid residues 602 to 651. Methods for obtaining MELK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a MELK. In further preferred embodiments, the fragment comprises the entire functionally active domain.

The term "MELK nucleic acid" refers to a DNA or RNA molecule that encodes a MELK polypeptide. Preferably, the MELK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human MELK. Methods of identifying orthologs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *C. elegans*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a MELK. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a MELK under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% FICOLL®, 1% BSA, and 500 μg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 μg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of MELK Nucleic Acids and Polypeptides MELK nucleic acids and polypeptides are useful for identifying and testing agents that modulate MELK function and for other applications related to the involvement of MELK in the RAC pathway. MELK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MELK protein for assays used to assess MELK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MELK is expressed in a cell line known to have defective RAC function. The recombinant cells are used in cell-based screening assay systems of the invention, as described further below.

The nucleotide sequence encoding a MELK polypeptide can be inserted into any appropriate expression vector. The necessary transcriptional and translational signals, including promoter/enhancer element, can derive from the native MELK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the MELK gene product, the expression vector can comprise a promoter operably linked to a MELK gene nucleic acid, one or more origins of replication, and, one or more selectable markers (e.g. thymidine kinase activity, resistance to antibiotics, etc.). Alternatively, recombinant expression vectors can be identified by assaying for the expression of the MELK gene product based on the physical or functional properties of the MELK protein in in vitro assay systems (e.g. immunoassays).

The MELK protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MELK gene sequence is identified, the gene product can be isolated and purified using standard methods (e.g. ion exchange, affinity, and gel exclusion chromatography; centrifugation; differential solubility; electrophoresis). Alternatively, native MELK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MELK or other genes associated with the RAC pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MELK expression may be used in in vivo assays to test for activity of a candidate RAC modulating agent, or to further assess the role of MELK in a RAC pathway process such as apoptosis or cell proliferation. Preferably, the altered MELK expression results in a detectable phenotype, such as decreased or increased levels of cell proliferation, angiogenesis, or apoptosis compared to control animals having normal MELK expression. The genetically modified animal may additionally have altered RAC expression (e.g. RAC knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MELK gene that results in a decrease of MELK function, preferably such that MELK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MELK gene is used to construct a homologous recombination vector suitable for altering an endogenous MELK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M B et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the MELK gene, e.g., by introduction of additional copies of MELK, or by operatively inserting a regulatory sequence that provides for altered expression of an endogenous copy of the MELK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the RAC pathway, as animal models of disease and disorders implicating defective RAC function, and for in vivo testing of candidate therapeutic agents, such as those identified in screens described below. The candidate therapeutic agents are administered to a genetically modified animal having altered MELK function and phenotypic changes are compared with appropriate control animals such as genetically modified animals that receive placebo treatment, and/or animals with unaltered MELK expression that receive candidate therapeutic agent.

In addition to the above-described genetically modified animals having altered MELK function, animal models having defective RAC function (and otherwise normal MELK function), can be used in the methods of the present invention. For example, a RAC knockout mouse can be used to assess, in vivo, the activity of a candidate RAC modulating agent identified in one of the in vitro assays described below. Preferably, the candidate RAC modulating agent when administered to a model system with cells defective in RAC function, produces a detectable phenotypic change in the model system indicating that the RAC function is restored, i.e., the cells exhibit normal cell cycle progression.

Modulating Agents

The invention provides methods to identify agents that interact with and/or modulate the function of MELK and/or the RAC pathway. Modulating agents identified by the methods are also part of the invention. Such agents are useful in a variety of diagnostic and therapeutic applications associated with the RAC pathway, as well as in further analysis of the MELK protein and its contribution to the RAC pathway. Accordingly, the invention also provides methods for modulating the RAC pathway comprising the step of specifically modulating MELK activity by administering a MELK-interacting or -modulating agent.

As used herein, a "MELK-modulating agent" is any agent that modulates MELK function, for example, an agent that interacts with MELK to inhibit or enhance MELK activity or otherwise affect normal MELK function. MELK function can be affected at any level, including transcription, protein expression, protein localization, and cellular or extra-cellular activity. In a preferred embodiment, the MELK-modulating agent specifically modulates the function of the MELK. The phrases "specific modulating agent", "specifically modulates", etc., are used herein to refer to modulating agents that directly bind to the MELK polypeptide or nucleic acid, and preferably inhibit, enhance, or otherwise alter, the function of the MELK. These phrases also encompass modulating agents that alter the interaction of the MELK with a binding partner, substrate, or cofactor (e.g. by binding to a binding partner of a MELK, or to a protein/binding partner complex, and altering MELK function). In a further preferred embodiment, the MELK-modulating agent is a modulator of the RAC pathway (e.g. it restores and/or upregulates RAC function) and thus is also a RAC-modulating agent.

Preferred MELK-modulating agents include small molecule compounds; MELK-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the MELK protein or may be identified by screening compound libraries. Alternative appropriate modulators of this class are natural products, particularly secondary metabolites from organisms such as plants or fungi, which can also be identified by screening compound libraries for MELK-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the RAC pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MELK-interacting proteins are useful in a variety of diagnostic and therapeutic applications related to the RAC pathway and related disorders, as well as in validation assays for other MELK-modulating agents. In a preferred embodiment, MELK-interacting proteins affect normal MELK function, including transcription, protein expression, protein localization, and cellular or extra-cellular activity. In another embodiment, MELK-interacting proteins are useful in detecting and providing information about the function of MELK proteins, as is relevant to RAC related disorders, such as cancer (e.g., for diagnostic means).

A MELK-interacting protein may be endogenous, i.e. one that naturally interacts genetically or biochemically with a MELK, such as a member of the MELK pathway that modulates MELK expression, localization, and/or activity. MELK-modulators include dominant negative forms of MELK-interacting proteins and of MELK proteins themselves. Yeast two-hybrid and variant screens offer preferred methods for identifying endogenous MELK-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An MELK-interacting protein may be an exogenous protein, such as a MELK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MELK antibodies are further discussed below.

In preferred embodiments, a MELK-interacting protein specifically binds a MELK protein. In alternative preferred embodiments, a MELK-modulating agent binds a MELK substrate, binding partner, or cofactor.

Antibodies

In another embodiment, the protein modulator is a MELK specific antibody agonist or antagonist. The antibodies have therapeutic and diagnostic utilities, and can be used in screening assays to identify MELK modulators. The antibodies can also be used in dissecting the portions of the MELK pathway responsible for various cellular responses and in the general processing and maturation of the MELK.

Antibodies that specifically bind MELK polypeptides can be generated using known methods. Preferably the antibody is specific to a mammalian ortholog of MELK polypeptide, and more preferably, to human MELK. Antibodies may be polyclonal, monoclonal (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Epitopes of MELK which are particularly antigenic can be selected, for example, by routine screening of MELK polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of a MELK. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of MELK or substantially purified fragments thereof. If MELK fragments are used, they preferably comprise at least 10, and more preferably, at least 20 contiguous amino acids of a MELK protein. In a particular embodiment, MELK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MELK-specific antibodies is assayed by an appropriate assay such as a solid phase enzyme-linked immunosorbant assay (ELISA®) using immobilized corresponding MELK polypeptides. Other assays, such as radio-immunoassays or fluorescent assays might also be used.

Chimeric antibodies specific to MELK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323:323-327). Humanized antibodies contain ~10% murine sequences and ~90% human sequences, and thus further reduce or eliminate immunogenicity, while retaining the antibody specificities (Co M S, and Queen C. 1991 Nature 351:501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

MELK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246:1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred MELK-modulating agents comprise nucleic acid molecules, such as antisense oligomers or double stranded RNA (dsRNA), which generally inhibit MELK activity. Preferred nucleic acid modulators interfere with the function of the MELK nucleic acid such as DNA replication, transcription, translocation of the MELK RNA to the site of protein translation, translation of protein from the MELK RNA, splicing of the MELK RNA to yield one or more mRNA species, or catalytic activity which may be engaged in or facilitated by the MELK RNA.

In one embodiment, the antisense oligomer is an oligonucleotide that is sufficiently complementary to a MELK mRNA to bind to and prevent translation, preferably by binding to the 5' untranslated region. MELK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred MELK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et a/, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a MELK-specific nucleic acid modulator is used in an assay to further elucidate the role of the MELK in the RAC pathway, and/or its relationship to other members of the pathway. In another aspect of the invention, a MELK-specific antisense oligomer is used as a therapeutic agent for treatment of RAC-related disease states.

Assay Systems

The invention provides assay systems and screening methods for identifying specific modulators of MELK activity. As used herein, an "assay system" encompasses all the components required for performing and analyzing results of an assay that detects and/or measures a particular event. In general, primary assays are used to identify or confirm a modulator's specific biochemical or molecular effect with respect to the MELK nucleic acid or protein. In general, secondary assays further assess the activity of a MELK modulating agent identified by a primary assay and may confirm that the modulating agent affects MELK in a manner relevant to the RAC pathway. In some cases, MELK modulators will be directly tested in a secondary assay.

In a preferred embodiment, the screening method comprises contacting a suitable assay system comprising a MELK polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates MELK activity, and hence the RAC pathway. The MELK polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of MELK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MELK-interacting proteins are used in screens to identify small molecule modulators, the binding specificity of the interacting protein to the MELK protein may be assayed by various known methods such as substrate processing (e.g. ability of the candidate MELK-specific binding agents to function as negative effectors in MELK-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit MELK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MELK polypeptide, a fusion protein thereof, or to cells or membranes bearing the polypeptide or fusion protein. The MELK polypeptide can be full length or a fragment thereof that retains functional MELK activity. The MELK polypeptide may be fused to another polypeptide, such as a peptide tag for detection or anchoring, or to another tag. The MELK polypeptide is preferably human MELK, or is an ortholog or derivative thereof as described above. In a preferred embodiment, the screening assay detects candidate agent-based modulation of MELK interaction with a binding target, such as an endogenous or exogenous protein or other substrate that has MELK-specific binding activity, and can be used to assess normal MELK gene function.

Suitable assay formats that may be adapted to screen for MELK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate MELK and RAC pathway modulators (e.g. U.S. Pat. No. 6,165,992 (kinase assays); U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Kinase assays. In some preferred embodiments the screening assay detects the ability of the test agent to modulate the kinase activity of a MELK polypeptide. In further embodiments, a cell-free kinase assay system is used to identify a candidate RAC modulating agent, and a secondary, cell-based assay, such as an apoptosis or hypoxia induction assay (described below), may be used to further characterize the candidate RAC modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma—$^{33}P$ ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radioligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Apoptosis assays. Apoptosis or programmed cell death is a suicide program that is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA® assay. The caspase 3/7 assay is based on the activation of the caspase cleavage activity as part of a cascade of events that occur during programmed cell death in many apoptotic pathways. In the caspase 3/7 assay (commercially available APO-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA® assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining the amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as ARRAYSCAN® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, and TOTO-3 fluorescent dye which labels DNA of dead cells with high cell membrane permeability.

An apoptosis assay system may comprise a cell that expresses a MELK, and that optionally has defective RAC function (e.g. RAC is over-expressed or under-expressed relative to wild-type cells). A test agent can be added to the apoptosis assay system and changes in induction of apoptosis relative to controls where no test agent is added, identify candidate RAC modulating agents. In some embodiments of the invention, an apoptosis assay may be used as a secondary assay to test a candidate RAC modulating agents that is initially identified using a cell-free assay system. An apoptosis assay may also be used to test whether MELK function plays a direct role in apoptosis. For example, an apoptosis assay may be performed on cells that over- or under-express MELK relative to wild type cells. Differences in apoptotic response compared to wild type cells suggests that the MELK plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CELLTITER 96® Aqueous Non-Radioactive Cell Proliferation Assay (Cat.#G5421).

Cell proliferation may also be assayed by colony formation in soft agar, or clonogenic survival assay (Sambrook et al., Molecular Cloning, Cold Spring Harbor (1989)). For example, cells transformed with MELK are seeded in soft agar plates, and colonies are measured and counted after two weeks incubation.

Cell proliferation may also be assayed by measuring ATP levels as indicator of metabolically active cells. Such assays are commercially available, for example CELL TITER-GLO™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a MELK may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses a MELK, and that optionally has defective RAC function (e.g. RAC is over-expressed or under-expressed relative to wild-type cells). A test agent can be added to the assay system and changes in cell proliferation or cell cycle relative to controls where no test agent is added, identify candidate RAC modulating agents. In some embodiments of the invention, the cell proliferation or cell cycle assay may be used as a secondary assay to test a candidate RAC modulating agents that is initially identified using another assay system such as a cell-free assay system. A cell proliferation assay may also be used to test whether MELK function plays a direct role in cell proliferation or cell cycle. For example, a cell proliferation or cell cycle assay may be performed on cells that over- or under-express MELK relative to wild type cells. Differences in proliferation or cell cycle compared to wild type cells suggests that the MELK plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in the presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses a MELK, and that optionally has defective RAC function (e.g. RAC is over-expressed or under-expressed relative to wild-type cells). A test agent can be added to the angiogenesis assay system and changes in angiogenesis relative to controls where no test agent is added, identify candidate RAC modulating agents. In some embodiments of the invention, the angiogenesis assay may be used as a secondary assay to test a candidate RAC modulating agents that is initially identified using another assay system. An angiogenesis assay may also be used to test whether MELK function plays a direct role in cell proliferation. For example, an angiogenesis assay may be performed on cells that over- or under-express MELK relative to wild type cells. Differences in angiogenesis compared to wild type cells suggest that the MELK plays a direct role in angiogenesis. U.S. Pat. Nos. 5,976,782, 6,225,118 and 6,444, 434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with MELK in hypoxic conditions (such as with 0.1% O2, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses a MELK, and that optionally has defective RAC function (e.g. RAC is over-expressed or under-expressed relative to wild-type cells). A test agent can be added to the hypoxic induction assay system and changes in hypoxic response relative to controls where no test agent is added, identify candidate RAC modulating agents. In some embodiments of the invention, the hypoxic induction assay may be used as a secondary assay to test a candidate RAC modulating agent that is initially identified using another assay system. A hypoxic induction assay may also be used to test whether MELK function plays a direct role in the hypoxic response. For example, a hypoxic induction assay may be performed on cells that over- or under-express MELK relative to wild type cells. Differences in hypoxic response compared to wild type cells suggest that the MELK plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Tubulogenesis. Tubulogenesis assays monitor the ability of cultured cells, generally endothelial cells, to form tubular structures on a matrix substrate, which generally simulates the environment of the extracellular matrix. Exemplary substrates include MATRIGEL™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpha. Thus, in a further preferred embodiment, a tubulogenesis assay system comprises testing a MELK's response to a variety of factors, such as FGF, VEGF, phorbol myristate acetate (PMA), TNF-alpha, ephrin, etc.

Cell Migration. An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing a MELK's response to a variety of pro-angiogenic factors, including tumor angiogenic and inflammatory angiogenic agents, and culturing the cells in serum free medium.

Sprouting assay. A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the MELK protein. Methods for testing antibody affinity and specificity are well known in the art (Harlow and Lane, 1988, 1999, supra). The enzyme-linked immunosorbant assay (ELISA®) is a preferred method for detecting MELK-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance MELK gene expression, preferably mRNA expression. In general, expression analysis comprises comparing MELK expression in like populations of cells (e.g., two pools of cells that endogenously or recombinantly express MELK) in the presence and absence of the nucleic acid modulator. Methods for analyzing mRNA and protein expression are well known in the art. For instance, Northern blotting, slot blotting, ribonuclease protection, quantitative RT-PCR (e.g., using the TAQMAN®, PE APPLIED BIOSYSTEMS®), or microarray analysis may be used to confirm that MELK mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the MELK protein or specific peptides. A variety of means including Western blotting, ELISA®, or in situ detection, are available (Harlow E and Lane D, 1988 and 1999, supra).

In some cases, screening assays described for small molecule modulators, particularly in assay systems that involve MELK mRNA expression, may also be used to test nucleic acid modulators.

Secondary Assays

Secondary assays may be used to further assess the activity of MELK-modulating agent identified by any of the above methods to confirm that the modulating agent affects MELK in a manner relevant to the RAC pathway. As used herein, MELK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MELK.

Secondary assays generally compare like populations of cells or animals (e.g., two pools of cells or animals that endogenously or recombinantly express MELK) in the presence and absence of the candidate modulator. In general, such assays test whether treatment of cells or animals with a candidate MELK-modulating agent results in changes in the RAC pathway in comparison to untreated (or mock- or placebo-treated) cells or animals. Certain assays use "sensitized genetic backgrounds", which, as used herein, describe cells or animals engineered for altered expression of genes in the RAC or interacting pathways.

Cell-Based Assays

Cell based assays may detect endogenous RAC pathway activity or may rely on recombinant expression of RAC pathway components. Any of the aforementioned assays may be used in this cell-based format. Candidate modulators are typically added to the cell media but may also be injected into cells or delivered by any other efficacious means.

Animal Assays

A variety of non-human animal models of normal or defective RAC pathway may be used to test candidate MELK modulators. Models for defective RAC pathway typically use genetically modified animals that have been engineered to mis-express (e.g., over-express or lack expression in) genes involved in the RAC pathway. Assays generally require systemic delivery of the candidate modulators, such as by oral administration, injection, etc.

In a preferred embodiment, RAC pathway activity is assessed by monitoring neovascularization and angiogenesis. Animal models with defective and normal RAC are used to test the candidate modulator's effect on MELK in MATRIGEL® assays. MATRIGEL® is an extract of basement membrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which over-express the MELK. The mixture is then injected subcutaneously (SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MELK is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the MELK endogenously are injected in the flank, $1\times10^5$ to $1\times10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a preexisting tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MIT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific MELK-modulating agents are useful in a variety of diagnostic and therapeutic applications where disease or disease prognosis is related to defects in the RAC pathway, such as angiogenic, apoptotic, or cell proliferation disorders. Accordingly, the invention also provides methods for modulating the RAC pathway in a cell, preferably a cell pre-determined to have defective or impaired RAC function (e.g. due to overexpression, underexpression, or misexpression of RAC, or due to gene mutations), comprising the step of administering an agent to the cell that specifically modulates MELK activity. Preferably, the modulating agent produces a detectable phenotypic change in the cell indicating that the RAC function is restored. The phrase "function is restored", and equivalents, as used herein, means that the desired phenotype is achieved, or is brought closer to normal compared to untreated cells. For example, with restored RAC function, cell proliferation and/or progression through cell cycle may normalize, or be brought closer to normal relative to untreated cells. The invention also provides methods for treating disorders or disease associated with impaired RAC function by administering a therapeutically effective amount of a MELK-modulating agent that modulates the RAC pathway. The invention further provides methods for modulating MELK function in a cell, preferably a cell pre-determined to have defective or impaired MELK function, by administering a MELK-modulating agent. Additionally, the invention provides a method for treating disorders or disease associated with impaired MELK function by administering a therapeutically effective amount of a MELK-modulating agent.

The discovery that MELK is implicated in RAC pathway provides for a variety of methods that can be employed for the diagnostic and prognostic evaluation of diseases and disorders involving defects in the RAC pathway and for the identification of subjects having a predisposition to such diseases and disorders.

Various expression analysis methods can be used to diagnose whether MELK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective RAC signaling that express a MELK, are identified as amenable to treatment with a MELK modulating agent. In a preferred application, the RAC defective tissue overexpresses a MELK relative to normal tissue. For example, a Northern blot analysis of mRNA from tumor and normal cell lines, or from tumor and matching normal tissue samples from the same patient, using full or partial MELK cDNA sequences as probes, can determine whether particular tumors express or overexpress MELK. Alternatively, the TAQMAN® is used for quantitative RT-PCR analysis of MELK expression in cell lines, normal tissues and tumor samples (PE APPLIED BIOSYSTEMS®).

Various other diagnostic methods may be performed, for example, utilizing reagents such as the MELK oligonucleotides, and antibodies directed against a MELK, as described above for: (1) the detection of the presence of MELK gene mutations, or the detection of either over- or under-expression of MELK mRNA relative to the non-disorder state; (2) the detection of either an over- or an under-abundance of MELK gene product relative to the non-disorder state; and (3) the detection of perturbations or abnormalities in the signal transduction pathway mediated by MELK.

Kits for detecting expression of MELK in various samples, comprising at least one antibody specific to MELK, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in MELK expression, the method comprising: a) obtaining a biological sample from the patient; b) contacting the sample with a probe for MELK expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

Examples

The following experimental section and examples are offered by way of illustration and not by way of limitation.

I. *C. elegans* RAC Screen

A genetic screen was designed to identify modifiers of the Rac signaling pathway that also affect cell migrations in *C. elegans*. The basis of this screen is the observation that ced-10 and mig-2 single mutants resemble wildtype worms in morphology and movement, whereas double mutants have strong morphological and movement defects. In the primary screen, the function of individual genes is inactivated by RNA interference (RNAi) in wildtype, ced-10 and mig-2 worms at the L4 stage. The progeny of the RNA treated animals are then examined for morphological and movement defects resembling those of the ced-10; mig-2 double mutant. All genes that give such a phenotype in a ced-10 or mig-2 mutant background but not in a wildtype background are then tested in a direct cell migration assay. In the cell migration assay, a subset of mechanosensory neurons known as AVM and ALM are scored for their final positions in the animal using a GFP marker expressed in these cells. This migration assay is done in both wildtype and a ced-10 or mig-2 mutant background. Since the AVM and ALM cells normally migrate and reach their final position during the first larval stage, scoring of position is done in later larval or adult stages. Those genes that cause short or misguided migrations of these neurons when inactivated in a wildtype or rac mutant background are potentially relevant for treatment of diseases that involve cell migrations. 4B260 was an identified modifier from the screen. Orthologs of 4B260 are referred to herein as MELK.

BLAST analysis (Altschul et al., supra) was employed to identify orthologs of 4B260. For example, representative sequence from MELK, GI#7661974 (SEQ ID NO:6), shares 38% amino acid identity with the C. elegans 4B260.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and dust (Remm M, and Sonnhammer E. Classification of transmembrane protein families in the Caenorhabditis elegans genome and identification of human orthologs. Genome Res. 2000 November; 10(11):1679-89) programs. For example, the kinase domain (PFAM 00069) of MELK from GI#7661974 (SEQ ID NO:6) is located at approximately amino acid residues 11-263. Further, the kinase associated domain 1 (PF02149) of the same protein is located approximately at amino acid residues 602 to 651.

II. High-Throughput In Vitro Fluorescence Polarization Assay

Fluorescently-labeled MELK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MELK activity.

III. High-Throughput In Vitro Binding Assay.

$^{33}$P-labeled MELK peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate RAC modulating agents.

IV. Immunoprecipitations and Immunoblotting

For coprecipitation of transfected proteins, $3 \times 10^6$ appropriate recombinant cells containing the MELK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 μl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified MELK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 μg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 μl. The reaction is initiated by the addition of $^{33}$P-gamma-ATP (0.5 μCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC$^{SM}$ (American Type Culture Collection, Manassas, Va. 20110-2209). Normal and tumor tissues were obtained from Impath, UC Davis, CLONTECH™, STRATAGENE®, Ardais, Genome Collaborative, and AMBION®.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng/μl.

Single stranded cDNA was then synthesized by reverse transcribing the RNA samples using random hexamers and 500 ng of total RNA per reaction, following protocol 4304965 of APPLIED BIOSYSTEMS® (Foster City, Calif.).

Primers for expression analysis using TAQMAN® assay (APPLIED BIOSYSTEMS®, Foster City, Calif.) were prepared according to the TAQMAN® protocols, and the following criteria: a) primer pairs were designed to span introns to eliminate genomic contamination, and b) each primer pair produced only one product. Expression analysis was performed using a 7900HT instrument.

TAQMAN® reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor–average(all normal samples)>2× STDEV(all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator.

Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| Gene Name | MELK |
|---|---|
| NA Seq ID | 1 |
| Breast | 67% |
| # of Pairs | 36 |
| Colon | 49% |
| # of Pairs | 41 |
| Head And Neck | 75% |
| # of Pairs | 12 |
| Kidney | 90% |
| # of Pairs | 20 |
| Liver | 89% |
| # of Pairs | 9 |
| Lung | 79% |
| # of Pairs | 42 |
| Lymphoma | 75% |
| # of Pairs | 4 |
| Ovary | 68% |
| # of Pairs | 19 |
| Pancreas | 75% |
| # of Pairs | 12 |
| Prostate | 50% |
| # of Pairs | 24 |
| Skin | 57% |
| # of Pairs | 7 |
| Stomach | 82% |
| # of Pairs | 11 |
| Testis | 29% |
| # of Pairs | 7 |
| Thyroid Gland | 58% |
| # of Pairs | 12 |
| Uterus | 77% |
| # of Pairs | 22 |

What is claimed is:

1. A method of identifying a RAS-related C3 botulinum toxin substrate (RAC) pathway modulating agent, said method comprising the steps of:
   (a) providing an assay system comprising a Maternal Embryonic Leucine Zipper Kinase (MELK) polypeptide comprising SEQ ID NO: 6 or nucleic acid encoding SEQ ID NO: 6, wherein the assay system is capable of detecting the activity or expression of MELK;
   (b) contacting the assay system with a test agent that modulates the activity or expression of MELK; and
   (c) determining the activity or expression of the MELK polypeptide or nucleic acid in the assay system in the presence or absence of the test agent of step (b), wherein a change in MELK activity or expression between the presence and absence of the test agent identifies the test agent as a candidate RAC pathway modulating agent;
   (d) providing a second assay system comprising cultured cells or a non-human animal expressing MELK capable of detecting a change in the RAC pathway,
   (e) contacting the second assay system with the test agent of step (b); and
   (f) measuring the RAC pathway in the presence or absence of the test agent, wherein the detection of a difference in the presence and absence of the test agent confirms the test agent as a RAC pathway modulating agent.

2. The method of claim 1 wherein the first assay system comprises cultured cells that express the MELK polypeptide.

3. The method of claim 2 wherein the cultured cells additionally have defective RAC function.

4. The method of claim 1 wherein the first assay system includes a screening assay comprising a MELK polypeptide, and the candidate test agent is a small molecule modulator.

5. The method of claim 4 wherein the screening assay is a kinase assay.

6. The method of claim 1 wherein the second assay system is selected from the group consisting of an apoptosis assay system, a cell proliferation assay system, an angiogenesis assay system, and a hypoxic induction assay system.

7. The method of claim 1 wherein the first assay system includes a binding assay comprising a MELK polypeptide and the candidate test agent is an antibody.

8. The method of claim 1 wherein the first assay system includes an expression assay comprising a MELK nucleic acid and the candidate test agent is a nucleic acid modulator.

9. The method of claim 8 wherein the nucleic acid modulator is an antisense oligomer.

10. The method of claim 8 wherein the nucleic acid modulator is a phosphothioate morpholino oligomer (PMO).

11. The method of claim 1 wherein the second assay system comprises cells defective in RAC function and is capable of detecting a phenotypic change in the model system that indicates that the RAC function is restored when compared relative to wild-type cells.

12. The method of claim 11 wherein the model system is a mouse model with defective RAC function.

* * * * *

SEQUENCE LISTING

```
<160> NUMBER OF SEQ ID NOS: 6

<210> SEQ ID NO 1
<211> LENGTH: 2470
<212> TYPE: DNA
<213> ORGANISM: Homo sapiens

<400> SEQUENCE: 1
ttggcgggcg gaagcggcca caacccggcg atcgaaaaga ttcttaggaa cgccgtacca      60
gccgcgtctc tcaggacagc aggcccctgt ccttctgtcg ggcgccgctc agccgtgccc     120 tccgccccctc aggttctttt tctaattcca aataaacttg caagaggact atgaaagatt   180
atgatgaact tctcaaatat tatgaattac atgaaactat tgggacaggt ggctttgcaa     240
aggtcaaact tgcctgccat atccttactg gagagatggt agctataaaa atcatggata     300
aaaacacact agggagtgat ttgccccgga tcaaaacgga gattgaggcc ttgaagaacc     360
tgagacatca gcatatatgt caactctacc atgtgctaga gacagccaac aaaatattca     420
tggttcttga gtactgccct ggaggagagc tgtttgacta tataatttcc caggatcgcc     480
```

-continued

| | |
|---|---|
| tgtcagaaga ggagacccgg gttgtcttcc gtcagatagt atctgctgtt gcttatgtgc | 540 |
| acagccaggg ctatgctcac agggacctca agccagaaaa tttgctgttt gatgaatatc | 600 |
| ataaattaaa gctgattgac tttggtctct gtgcaaaacc caagggtaac aaggattacc | 660 |
| atctacagac atgctgtggg agtctggctt atgcagcacc tgagttaata caaggcaaat | 720 |
| catatcttgg atcagaggca gatgtttgga gcatgggcat actgttatat gttcttatgt | 780 |
| gtggatttct accatttgat gatgataatg taatggcttt atacaagaag attatgagag | 840 |
| gaaaatatga tgttcccaag tggctctctc ccagtagcat tctgcttctt caacaaatgc | 900 |
| tgcaggtgga cccaaagaaa cggatttcta tgaaaaatct attgaaccat ccctggatca | 960 |
| tgcaagatta caactatcct gttgagtggc aaagcaagaa tccttttatt cacctcgatg | 1020 |
| atgattgcgt aacagaactt tctgtacatc acagaaacaa caggcaaaca atggaggatt | 1080 |
| taatttcact gtggcagtat gatcacctca cggctaccta tcttctgctt ctagccaaga | 1140 |
| aggctcgggg aaaaccagtt cgtttaaggc tttcttcttt ctcctgtgga caagccagtg | 1200 |
| ctaccccatt cacagacatc aagtcaaata attggagtct ggaagatgtg accgcaagtg | 1260 |
| ataaaaatta tgtggcggga ttaatagact atgattggtg tgaagatgat ttatcaacag | 1320 |
| gtgctgctac tccccgaaca tcacagttta ccaagtactg gacagaatca aatggggtgg | 1380 |
| aatctaaatc attaactcca gccttatgca gaacacctgc aaataaatta agaacaaag | 1440 |
| aaaatgtata tactcctaag tctgctgtaa agaatgaaga gtactttatg tttcctgagc | 1500 |
| caaagactcc agttaataag aaccagcata agagagaaat actcactacg ccaaatcgtt | 1560 |
| acactacacc ctcaaaagct agaaaccagt gcctgaaaga aactccaatt aaaataccag | 1620 |
| taaattcaac aggaacagac aagttaatga caggtgtcat tagccctgag aggcggtgcc | 1680 |
| gctcagtgga attggatctc aaccaagcac atatggagga gactccaaaa agaaagggag | 1740 |
| ccaaagtgtt tgggagcctt gaaggggggt tggataaggt tatcactgtg ctcaccagga | 1800 |
| gcaaaaggaa gggttctgcc agagacgggc ccagaagact aaagcttcac tataatgtga | 1860 |
| ctacaactag attagtgaat ccagatcaac tgttgaatga aataatgtct attcttccaa | 1920 |
| agaagcatgt tgactttgta caaaagggtt atacactgaa gtgtcaaaca cagtcagatt | 1980 |
| ttgggaaagt gacaatgcaa tttgaattag aagtgtgcca gcttcaaaaa cccgatgtgg | 2040 |
| tgggtatcag gaggcagcgg cttaagggcg atgcctgggt ttacaaaaga ttagtggaag | 2100 |
| acatcctatc tagctgcaag gtataattga tggattcttc catcctgccg gatgagtgtg | 2160 |
| ggtgtgatac agcctacata aagactgtta tgatcgcttt gattttaaag ttcattggaa | 2220 |
| ctaccaactt gtttctaaag agctatctta agaccaatat ctctttgttt ttaaacaaaa | 2280 |
| gatattattt tgtgtatgaa tctaaatcaa gcccatctgt cattatgtta ctgtctttt | 2340 |
| taatcatgtg gttttgtata ttaataattg ttgactttct tagattcact tccatatgtg | 2400 |
| aatgtaagct cttaactatg tctctttgta atgtgtaatt tctttctgaa ataaaaccat | 2460 |
| ttgtgaatat | 2470 |

<210> SEQ ID NO 2
<211> LENGTH: 2510
<212> TYPE: DNA
<213> ORGANISM: Homo sapiens

<400> SEQUENCE: 2

| | |
|---|---|
| ggcacgaggc gaaaagattc ttaggaacgc cgtaccagcc gcgtctctca ggacagcagg | 60 |
| cccctgtcct tctgtcgggc gccgctcagc cgtgccctcc gccccctcagg ttcttttct | 120 |

```
aattccaaat aaacttgcaa gaggactatg aaagattatg atgaacttct caaatattat       180
gaattacatg aaactattgg gacaggtggc tttgcaaagg tcaaacttgc ctgccatatc      240
cttactggag agatggtagc tataaaaatc atggataaaa acacactagg gagtgatttg      300
ccccggatca aaacggagat tgaggccttg aagaacctga acatcagca tatatgtcaa       360 ctctaccatg tgctagagac agccaacaaa atattcatgg ttcttgagta ctgccctgga      420
ggagagctgt ttgactatat aatttcccag gatcgcctgt cagaagagga gacccgggtt     480
gtcttccgtc agatagtatc tgctgttgct tatgtgcaca gccagggcta tgctcacagg     540
gacctcaagc cagaaaattt gctgtttgat gaatatcata aattaaagct gattgacttt      600
ggtctctgtg caaacccaa gggtaacaag gattaccatc tacagacatg ctgtgggagt      660
ctggcttatg cagcacctga gttaatacaa ggcaaatcat atcttggatc agaggcagat     720
gtttggagca tgggcatact gttatatgtt cttatgtgtg gatttctacc atttgatgat     780
gataatgtaa tggctttata caagaagatt atgagaggaa aatatgatgt tcccaagtgg     840
ctctctccca gtagcattct gcttcttcaa caaatgctgc aggtggaccc aaagaaacgg     900
atttctatga aaaatctatt gaaccatccc tggatcatgc aagattacaa ctatcctgtt     960
gagtggcaaa gcaagaatcc ttttattcac ctcgatgatg attgcgtaac agaacttct    1020 gtacatcaca gaaacaacag gcaaacaatg gaggatttaa tttcactgtg gcagtatgat   1080
cacctcacgg ctacctatct tctgcttcta gccaagaagg ctcggggaaa accagttcgt   1140
ttaaggcttt cttcttttctc ctgtggacaa gccagtgcta ccccattcac agacatcaag   1200
tcaaataatt ggagtctgga agatgtgacc gcaagtgata aaaattatgt ggcgggatta   1260
atagactatg attggtgtga agatgattta tcaacaggtg ctgctactcc ccgaacatca   1320
cagtttacca agtactggac agaatcaaat ggggtggaat ctaaatcatt aactccagcc   1380
ttatgcagaa cacctgcaaa taattaaag aacaaagaaa atgtatatac tcctaagtct    1440
gctgtaaaga atgaagagta ctttatgttt cctgagccaa agactccagt taataagaac   1500
cagcataaga gagaaatact cactacgcca atcgttaca ctacaccctc aaaagctaga    1560
aaccagtgcc tgaaagaaac tccaattaaa ataccagtaa attcaacagg aacagacaag   1620
ttaatgacag gtgtcattag ccctgagagg cggtgccgct cagtggaatt ggatctcaac   1680
caagcacata tggaggagac tccaaaaaga aagggagcca aagtgtttgg gagccttgaa   1740
agggggttgg ataaggttat cactgtgctc accaggagca aaaggaaggg ttctgccaga   1800
gacgggccca aaagactaaa gcttcactat aatgtgacta caactagatt agtgaatcca   1860
gatcaactgt tgaatgaaat aatgtctatt cttccaaaga agcatgttga cttgtacaa     1920 aagggttata cactgaagtg tcaaacacag tcagattttg ggaaagtgac aatgcaattt    1980
gaattagaag tgtgccagct tcaaaaaccc gatgtggtgg gtatcaggag gcagcggctt   2040
aagggcgatg cctgggttta caaaagatta gtggaagaca tcctatctag ctgcaaggta   2100
taattgatgg attcttccat cctgccggat gagtgtgggt gtgatacagc ctacataaag   2160
actgttatga tcgctttgat tttaaagttc attggaacta ccaacttgtt tctaaagagc   2220
tatcttaaga ccaatatctc tttgttttta aacaaaagat attatttttgt gtatgaatct   2280 aaatcaagcc catctgtcat tatgttactg tcttttttaa tcatgtggtt ttgtatatta   2340
ataattgttg actttcttag attcacttcc atatgtgaat gtaagctctt aactatgtct   2400
ctttgtaatg tgtaattct ttctgaaata aaaccatttg tgaatataaa aaaaaaaa       2460 aaaaaaaaaa aaaaaaaaaa aaaaaaaaaa aaaaaaaaaa aaaaaaaaa                 2510
```

<210> SEQ ID NO 3
<211> LENGTH: 2158
<212> TYPE: DNA
<213> ORGANISM: Homo sapiens

<400> SEQUENCE: 3

```
gctagcgcta ccggactcag atctatttag gtgacactat agaagagcca agctgctcga      60
gccgccacca tggactacaa ggacgatgac gataagggat ccaaagatta tgatgaactt     120
ctcaaatatt atgaattaca tgaaactatt gggacaggtg gctttgcaaa ggtcaaactt     180
gcctgccata tccttactgg agagatggta gctataaaaa tcatggataa aaacacacta     240
gggagtgatt tgccccggat caaaacggag attgaggcct tgaagaacct gagacatcag     300
catatatgtc aactctacca tgtgctagag acagccaaca aatattcat ggttcttgag      360
tactgccctg gaggagagct gtttgactat ataatttccc aggatcgcct gtcagaagag     420
gagacccggg ttgtcttccg tcagatagta tctgctgttg cttatgtgca cagccagggc     480
tatgctcaca gggacctcaa gccagaaaat ttgctgtttg atgaatatca taaattaaag     540
ctgattgact ttggtctctg tgcaaaaccc aagggtaaca aggattacca tctacagaca     600
tgctgtggga gtctggctta tgcagcacct gagttaatac aaggcaaatc atatcttgga     660
tcagaggcag atgtttggag catgggcata ctgttatatg ttcttatgtg tggatttcta     720
ccatttgatg atgataatgt aatggcttta acaagaaga ttatgagagg aaaatatgat      780
gttcccaagt ggctctctcc cagtagcatt ctgcttcttc aacaaatgct gcaggtggac     840
ccaaagaaac ggatttctat gaaaaatcta ttgaaccatc cctggatcat gcaagattac     900
aactatcctg ttgagtggca agcaagaat ccttttattc acctcgatga tgattgcgta      960
acagaacttt ctgtacatca cagaaacaac aggcaaacaa tggaggattt aatttcactg    1020
tggcagtatg atcacctcac ggctaccat cttctgcttc tagccaagaa ggctcgggga     1080
aaaccagttc gtttaaggct tcttcttttc tcctgtggac aagccagtgc taccccattc    1140
acagacatca gtcaaataa ttggagtctg aagatgtga ccgcaagtaa taaaaattat       1200
gtggcgggat taatagacta tgattggtgt gaagatgatt tatcaacagg tgctgctact    1260
ccccgaacat cacagtttac caagtactgg acagaatcaa atggggtgga atctaaatca    1320
ttaactccag ccttatgcag aacacctgca ataaattaa agaacaaaga aaatgtatat     1380
actcctaagt ctgctgtaaa gaatgaagag tactttatgt ttcctgagcc aaagactcca    1440
gttaataaga accagcataa gagagaaata ctcactacgc caaatcgtta cactacaccc    1500
tcaaaagcta gaaccagtg cctgaaagaa actccaatta aataccagt aaattcaaca      1560
ggaacagaca agttatgac aggtgtcatt agccctgaga ggcggtgccg ctcagtggaa     1620
ttggatctca accaagcaca tatggaggag actccaaaaa gaagggagc caaagtgttt     1680
gggagccttg aaaggggggtt ggataaggtt atcactgtgc tcaccaggag caaaaggaag    1740
ggttctgcca gagacgggcc cagaagacta aagcttcact ataatgtgac tacaactaga    1800
ttagtgaatc cagatcaact gttgaatgaa ataatgtcta ttcttccaaa gaagcatgtt    1860
gactttgtac aaaagggtta tacactgaag tgtcaaacac agtcagattt gggaaagtg     1920
acaatgcaat tgaattaga agtgtgccag cttcaaaaac ccgatgtggt gggtatcagg    1980
aggcagcggc ttaagggcga tgcctgggtt tacaaaagat tagtggaaga catcctatct    2040
agctgcaagg tagaattctg ataatgagcg gccgcctcgg ccaaacatcg ataaaataaa    2100
agattttatt tagtctccag aaaaagggggg gaatgaaaga ccccacctgt aggtttgg    2158
```

<210> SEQ ID NO 4
<211> LENGTH: 1734
<212> TYPE: DNA
<213> ORGANISM: Homo sapiens

<400> SEQUENCE: 4

| tatttaggtg | acactataga | agagccaagc | tgctcgagcc | gccaccatgg | actacaagga | 60 |
| cgatgacgat | aagggatcca | agattatga | tgaacttctc | aaatattatg | aattacatga | 120 |
| aactattggg | acaggtggct | ttgcaaaggt | caaacttgcc | tgccatatcc | ttactggaga | 180 |
| gatggtagct | ataaaaatca | tggataaaaa | cacactaggg | agtgatttgc | cccggatcaa | 240 |
| aacggagatt | gaggccttga | agaacctgag | acatcagcat | atatgtcaac | tctaccatgt | 300 |
| gctagagaca | gccaacaaaa | tattcatggt | tcttgagggt | aacaaggatt | accatctaca | 360 |
| gacatgctgt | gggagtctgg | cttatgcagc | acctgagtta | atacaaggca | aatcatatct | 420 |
| tggatcagag | gcagatgttt | ggagcatggg | catactgtta | tatgttctta | tgtgtggatt | 480 |
| tctaccattt | gatgatgata | atgtaatggc | tttatacaag | aagattatga | gaggaaaata | 540 |
| tgatgttccc | aagtggctct | ctcccagtag | cattctgctt | cttcaacaaa | tgctgcaggt | 600 |
| ggacccaaag | aaacggattt | ctatgaaaaa | tctattgaac | catccctgga | tcatgcaaga | 660 |
| ttacaactat | cctgttgagt | ggcaaagcaa | gaatcctttt | attcacctcg | atgatgattg | 720 |
| cgtaacagaa | ctttctgtac | atcacagaaa | caacaggcaa | acaatggagg | atttaatttc | 780 |
| actgtggcag | tatgatcacc | tcacggctac | ctatcttctg | cttctagcca | agaaggctcg | 840 |
| gggaaaacca | gttcgtttaa | ggcttctctt | tttctcctgt | ggacaagcca | gtgctacccc | 900 |
| attcacagac | atcaagttta | ccaagtactg | gacagaatca | aatggggtgg | aatctaaatc | 960 |
| attaactcca | gccttatgca | gaacacctgc | aaataaatta | agaacaaag | aaaatgtata | 1020 |
| tactcctaag | tctgctgtaa | agaatgaaga | gtactttatg | tttcctgagc | caaagactcc | 1080 |
| agttaataag | aaccagcata | agagagaaat | actcactacg | ccaaatcgtt | acactacacc | 1140 |
| ctcaaaagct | agaaaccagt | gcctgaaaga | aactccaatt | aaaataccag | taaattcaac | 1200 |
| aggaacagac | aagttaatga | caggtgtcat | tagccctgag | aggcggtgcc | gctcagtgga | 1260 |
| attggatctc | aaccaagcac | atatggagga | gactccaaaa | agaaagggag | ccaaagtgtt | 1320 |
| tgggagcctt | gaaaggggt | tggataaggt | tatcactgtg | ctcaccagga | gcaaaaggaa | 1380 |
| gggttctgcc | agagacgggc | ccagaagact | aaagcttcac | tataatgtga | ctacaactag | 1440 |
| attagtgaat | ccagatcaac | tgttgaatga | aataatgtct | attcttccaa | agaagcatgt | 1500 |
| tgactttgta | caaaagggtt | atacactgaa | gtgtcaaaca | cagtcagatt | ttgggaaagt | 1560 |
| gacaatgcaa | tttgaattag | aagtgtgcca | gcttcaaaaa | cccgatgtgg | tgggtatcag | 1620 |
| gaggcagcgg | cttaagggcg | atgcctgggt | ttacaaaaga | ttagtggaag | acatcctatc | 1680 |
| tagctgcaag | gtagaattct | gataatgagc | ggccgcctcg | gccaaacatc | gata | 1734 |

<210> SEQ ID NO 5
<211> LENGTH: 2501
<212> TYPE: DNA
<213> ORGANISM: Homo sapiens

<400> SEQUENCE: 5

| cgaaaagatt | cttaggaacg | ccgtaccagc | cgcgtctctc | aggacagcag | gcccctgtcc | 60 |
| ttctgtcggg | cgccgctcag | ccgtgccctc | cgccctcag | gttcttttc | taattccaaa | 120 |
| taaacttgca | agaggactat | gaaagattat | gatgaacttc | tcaaatatta | tgaattacat | 180 |

```
gaaactattg ggacaggtgg ctttgcaaag gtcaaacttg cctgccatat ccttactgga    240
gagatggtag ctataaaaat catggataaa aacacactag ggagtgattt gccccggatc    300
aaaacggaga ttgaggcctt gaagaacctg agacatcagc atatatgtca actctaccat    360
gtgctagaga cagccaacaa aatattcatg gttcttgagt actgccctgg aggagagctg    420
tttgactata taatttccca ggatcgcctg tcagaagagg agacccgggt tgtcttccgt    480
cagatagtat ctgctgttgc ttatgtgcac agccagggct atgctcacag ggacctcaag    540
ccagaaaatt tgctgtttga tgaatatcat aaattaaagc tgattgactt tggtctctgt    600
gcaaacccca agggtaacaa ggattaccat ctacagacat gctgtgggag tctggcttat    660
gcagcacctg agttaataca aggcaaatca tatcttggat cagaggcaga tgtttggagc    720
atgggcatac tgttatatgt tcttatgtgt ggatttctac catttgatga tgataatgta    780
atggctttat acaagaagat tatgagagga aaatatgatg ttcccaagtg gctctctccc    840
agtagcattc tgcttcttca acaaatgctg caggtggacc caaagaaacg gatttctatg    900
aaaaatctat tgaaccatcc ctggatcatg caagattaca actatcctgt tgagtggcaa    960
agcaagaatc ttttattca cctcgatgat gattgcgtaa cagaactttc tgtacatcac   1020
agaaacaaca ggcaaacaat ggaggattta atttcactgt ggcagtatga tcacctcacg   1080
gctacctatc ttctgcttct agccaagaag gctcggggaa aaccagttcg tttaaggctt   1140
tcttctttct cctgtggaca agccagtgct accccattca cagacatcaa gtcaaataat   1200
tggagtctgg aagatgtgac cgcaagtgat aaaaattatg tggcgggatt aatagactat   1260
gattggtgtg aagatgattt atcaacaggt gctgctactc cccgaacatc acagtttacc   1320
aagtactgga cagaatcaaa tggggtggaa tctaaatcat taactccagc cttatgcaga   1380
acacctgcaa ataaattaaa gaacaaagaa aatgtatata ctcctaagtc tgctgtaaag   1440
aatgaagagt actttatgtt tcctgagcca aagactccag ttaataagaa ccagcataag   1500
agagaaatac tcactacgcc aaatcgttac actacaccct caaaagctag aaaccagtgc   1560
ctgaaagaaa ctccaattaa aataccagta aattcaacag gaacagacaa gttaatgaca   1620
ggtgtcatta gccctgagag gcggtgccgc tcagtggaat tggatctcaa ccaagcacat   1680
atggaggaga ctccaaaaag aaagggagcc aaagtgtttg ggagccttga aaggggggttg   1740
gataaggtta tcactgtgct caccaggagc aaaaggaagg gttctgccag agacgggccc   1800
agaagactaa agcttcacta taatgtgact acaactagat tagtgaatcc agatcaactg   1860
ttgaatgaaa taatgtctat tcttccaaag aagcatgttg actttgtaca aaagggttat   1920
acactgaagt gtcaaacaca gtcagatttt gggaaagtga caatgcaatt tgaattagaa   1980
gtgtgccagc ttcaaaaacc cgatgtgtg ggtatcagga ggcagcggct taagggcgat   2040
gcctgggttt acaaaagatt agtggaagac atcctatcta gctgcaaggt ataattgatg   2100
gattcttcca tcctgccgga tgagtgtggg tgtgatacag cctacataaa gactgttatg   2160
atcgctttga ttttaaagtt cattggaact accaacttgt ttctaaagag ctatcttaag   2220
accaatatct ctttgttttt aaacaaaaga tattattttg tgtatgaatc taaatcaagc   2280
ccatctgtca ttatgttact gtcttttta atcatgtggt tttgtatatt aataattgtt   2340
gactttctta gattcacttc catatgtgaa tgtaagctct taactatgtc tctttgtaat   2400
gtgtaatttc tttctgaaat aaaaccattt gtgaatataa aaaaaaaaa aaaaaaaaa   2460
aaaaaaaaaa aaaaaaaaaa aaaaaaaaa aaaaaaaaa a                         2501
```

<210> SEQ ID NO 6
<211> LENGTH: 651
<212> TYPE: PRT
<213> ORGANISM: Homo sapiens

<400> SEQUENCE: 6

```
Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Ser Asp Leu Pro Arg Ile Lys Thr Glu Ile Glu Ala Leu Lys Asn Leu
    50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
    130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
    210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Cys Val Thr
        275                 280                 285

Glu Leu Ser Val His His Arg Asn Asn Arg Gln Thr Met Glu Asp Leu
    290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
                325                 330                 335

Phe Ser Cys Gly Gln Ala Ser Ala Thr Pro Phe Thr Asp Ile Lys Ser
            340                 345                 350

Asn Asn Trp Ser Leu Glu Asp Val Thr Ala Ser Asp Lys Asn Tyr Val
        355                 360                 365

Ala Gly Leu Ile Asp Tyr Asp Trp Cys Glu Asp Asp Leu Ser Thr Gly
    370                 375                 380

Ala Ala Thr Pro Arg Thr Ser Gln Phe Thr Lys Tyr Trp Thr Glu Ser
```

-continued

```
            385                 390                 395                 400
Asn Gly Val Glu Ser Lys Ser Leu Thr Pro Ala Leu Cys Arg Thr Pro
                        405                 410                 415

Ala Asn Lys Leu Lys Asn Lys Glu Asn Val Tyr Thr Pro Lys Ser Ala
                420                 425                 430

Val Lys Asn Glu Glu Tyr Phe Met Phe Pro Glu Pro Lys Thr Pro Val
        435                 440                 445

Asn Lys Asn Gln His Lys Arg Glu Ile Leu Thr Thr Pro Asn Arg Tyr
    450                 455                 460

Thr Thr Pro Ser Lys Ala Arg Asn Gln Cys Leu Lys Glu Thr Pro Ile
465                 470                 475                 480

Lys Ile Pro Val Asn Ser Thr Gly Thr Asp Lys Leu Met Thr Gly Val
                485                 490                 495

Ile Ser Pro Glu Arg Arg Cys Arg Ser Val Glu Leu Asp Leu Asn Gln
                500                 505                 510

Ala His Met Glu Glu Thr Pro Lys Arg Lys Gly Ala Lys Val Phe Gly
            515                 520                 525

Ser Leu Glu Arg Gly Leu Asp Lys Val Ile Thr Val Leu Thr Arg Ser
    530                 535                 540

Lys Arg Lys Gly Ser Ala Arg Asp Gly Pro Arg Arg Leu Lys Leu His
545                 550                 555                 560

Tyr Asn Val Thr Thr Thr Arg Leu Val Asn Pro Asp Gln Leu Leu Asn
                565                 570                 575

Glu Ile Met Ser Ile Leu Pro Lys Lys His Val Asp Phe Val Gln Lys
                580                 585                 590

Gly Tyr Thr Leu Lys Cys Gln Thr Gln Ser Asp Phe Gly Lys Val Thr
            595                 600                 605

Met Gln Phe Glu Leu Glu Val Cys Gln Leu Gln Lys Pro Asp Val Val
        610                 615                 620

Gly Ile Arg Arg Gln Arg Leu Lys Gly Asp Ala Trp Val Tyr Lys Arg
625                 630                 635                 640

Leu Val Glu Asp Ile Leu Ser Ser Cys Lys Val
                645                 650
```